United States Patent
Ziegler et al.

(10) Patent No.: US 6,291,668 B1
(45) Date of Patent: Sep. 18, 2001

(54) OLIGONUCLEOTIDE DERIVATIVES

(75) Inventors: Annemarie Ziegler, Santiago (CL);
Uwe Zangemeister-Wittke,
Hohentengen (DE); Doriano Fabbro,
Arlesheim (CH); Karl-Heinz Altmann,
Reinach (CH)

(73) Assignee: Novartis AG, Basel (CH)

( * ) Notice: Subject to any disclaimer, the term of this patent is extended or adjusted under 35 U.S.C. 154(b) by 0 days.

(21) Appl. No.: 09/445,486

(22) PCT Filed: Jun. 5, 1998

(86) PCT No.: PCT/EP98/03362

§ 371 Date: Dec. 7, 1999

§ 102(e) Date: Dec. 7, 1999

(87) PCT Pub. No.: WO98/56905

PCT Pub. Date: Dec. 17, 1998

(30) Foreign Application Priority Data

Jun. 9, 1997 (GB) .................................................. 9711919

(51) Int. Cl.$^7$ .................................................. C07H 21/04
(52) U.S. Cl. ....................... 536/24.5; 536/23.1; 536/24.3; 536/24.31; 536/24.33
(58) Field of Search .................................. 536/23.1, 24.3, 536/24.31, 24.33, 24.5; 435/91.1, 6, 325, 375; 514/44

(56) References Cited

U.S. PATENT DOCUMENTS 5,734,033 * 3/1998 Reed .................................. 536/23.1

FOREIGN PATENT DOCUMENTS

WO 93/20200  10/1993  (WO) .
WO 93/24653  12/1993  (WO) .
WO 95/03788   2/1995  (WO) .
WO 95/08350   3/1995  (WO) .
WO 96/27663   9/1996  (WO) .

OTHER PUBLICATIONS

Andrea D. Branch, A good antisense molecule is hard to find , TIBS, 47–48, Feb. 1998.*
Stanley Crooke, Antisense Research and Applications, Chapter 1, Basic Principles of Antisense Therapeutics, Springer–Verlag Press, Berlin, Heidelberg, New York, p. 3, Jul. 1998.*
Martin P., Helvetica Chimica Acto, vol. 78, pp. 486–504, Feb. 1998.*
Campos et al., Blood, vol. 84 (2), "Effects of BCL–2 Antisense Oligodeoxynucleotides on In Vitro Proliferation and Survival of Normal Marrow Progenitors and Leukemic Cells," pp. 595–600 (1994).
Chomczynski and Sacchi, Analytical Biochemistry, vol. 162, "Single–Step Method of RNA Isolation by Acid Guanidinium Thiocyanate–Phenol–Chloroform Extraction," pp. 156–159 (1987).

Cotter F.E. et al., Oncogene, vol. 9, "Antisense oligonucleotides suppress B–cell lymphona growth in a SCID–hu mouse model," pp. 3049–3055 (1994).
Cotter T.G. et al., Cancer Research, vol. 52, "Microfilament–disrupting Agents Prevent the Formation of Apoptotic Bodies in Tumor Cells Undergoing Apoptosis," pp. 997–1005 (1992).
Crooke S.T., Therapeutic Applications of Oligonucleotides, 1995, R. G. Landes Company, Austin, TX—Text index provided.
DeMesmaeker A. et al., Acc. Chem. Res., vol. 28, "Antisense Oligonucleotides," pp. 366–374 (1995).
DeMesmaeker A. et al., Current Opinion in Structural Biology, vol. 5, "Backbone modifications in oligonucleotides and peptide nucleic acid systems," pp. 343–355 (1995).
Dole M. et al., Cancer Research, vol. 54, "Bcl–2 Inhibits Chemotherapy–induced Apoptosis in Neuroblastoma," pp. 3253–3259 (1994).
Epstein F. (Ed.), Oligonucleotides and Analogues, 1991, Oxford University Press, Oxford, U.K.—Text index provided.
Fukunaga–Johnson N. et al., Carcinogenesis, vol. 16 (8), "Bcl–2 protects murine erythroleukemia cells from p53–dependent and –independent radiation–induced cell death," pp. 1761–1767 (1995).
Gait M.J. et al., Oligonucleotides and Analogues—A Practical Approach, F. Eckstein (Ed.), "Oligoribonucleotide synthesis," pp. 25–48, Oxford University Press (1991).
Hanada M. et al., Cancer Research, vol. 53, "Regulation of Bcl–2 Oncoprotein Levels with Differentiation of Human Neuroblastoma Cells," pp. 4978–4986 (1993).
Hockenbery D. et al., Nature, vol. 348, "Bcl–2 is an inner mitochondrial membrane protein that blocks programmed cell death," pp. 334–336 (1990).
Ikegaki N., Cancer Research, vol. 54, "Expression of bcl–2 in Small Cell Lung Carcinoma Cells," pp. 6–8 (1994).
Jiang Shi–Xu et al., Journal of Pathology, vol. 177, "Expression of bcl–2 Oncogene Protein is Prevalent in Small Cell Lung Carcinomas," pp. 135–138 (1995).

(List continued on next page.)

Primary Examiner—John L. LeGuyader
Assistant Examiner—Janet Epps
(74) Attorney, Agent, or Firm—Hesna J. Pfeiffer

(57) ABSTRACT

The present invention relates to an oligonucleotide derivative which is specifically hybridizable to a region of a RNA deriving from the gene encoding human Bcl-2 protein, the region being selected from the group consisting of a region comprising a sequence corresponding to a sequence ranging from base position no. 1880 (5') to no. 1899 (3'), or comprising at least a part thereof, of the human Bcl-2 cDNA, and a region comprising the translation termination codon of the RNA.

2 Claims, No Drawings

OTHER PUBLICATIONS

Keith F. J. et al., Leukemia, vol. (9), "Inhibition of bcl–2 with Antisense Oligonucleotides Induces Apoptosis and Increases the Sensitivity of AML Blasts to Ara–C," pp. 131–138 (1995).

Kitada S. et al., Antisense Research and Development, vol. 4, "Reversal of Chemoresistance of Lymphoma Cells by Antisense–Mediated Reduction of bcl–2 Gene Expression," pp. 71–79 (1994).

Luedke G.H. et al., Proceedings of the American Association for Cancer Research, vol. 38, "Antisense oligonucleotides targeting sequences shared by the Bcl–2 and the Bcl–xl mRNA efficiently downregulate expression of both proteins and induce apoptosis of lung cancer cells," p. 170 (1997).

Martin P., Helvetica Chimica Acta, vol. 78, "A New Access to 2 –0–Alkylated Ribonuclesides and Properties of 2 – 0–Alkylated Oligoribonucleotides," pp. 486–504 (1995) Article in German with English Abstract.

Nicoletti I. et al., Journal of Immunological Methods, vol. 139, "A rapid and simple method for measuring thymocyte apoptosis by propidium iodide staining and flow cytometry," pp. 271–279 (1991).

Oberhammer F. et al., The EMBO Journal, vol. 12 (9), "Apoptotic death in epithelial cells: cleavage of DNA to 300 and/or 50 kb fragments prior to or in the absence of internucleosomal fragmentation," pp. 3679–3684 (1993).

Ohmori T. et al., Biochemical and Biophysical Research Communications, vol. 192 (1), "Apoptosis of Lung Cancer Cells Caused by Some Anti–Cancer Agents (MMC, CPT–11, ADM) is Inhibited by BCL–2," pp. 30–36 (1993).

Reed J.C. et al., Annals of Oncology, vol. 5, "Regulation of chemoresistance by the bcl–2 oncoprotein in non–Hodgkin's lymphoma and lymphocytic leukemia cell lines," pp. 561–565 (1994).

"Analysis and Cloning of Eukaryotic Genomic DNA," in *Molecular Cloning—A Laboratory Manual*, Sambrook, Fritsch and Maniatis (Eds.), pp. 9.47–9.58, Cold Spring Harbor Laboratory Press (1989).

Sanghvi and Cook (Eds.), *Carbohydrate Modifications in Antisense Research*, ACS Symposium Series, American Chemical Society, Developed from a symposium sponsored at the 207th National Meeting of the American Chemical Society, pp. v–vii (Mar. 13–17, 1994)—preface and table of contents provided only.

Sanghvi Y., "Heterocyclic Base Modifications in Nucleic Acids and their Applications in Antisense Oligonucleotides," in *Antisense Research and Applications*, Crooke S.T. and Lebleu B. (Eds.), pp. 273–288, CRC Press, Inc. (1993).

Sinha and Striepeke, *Oligonucleotides and Analogues—A Practical Approach*, F. Eckstein (Ed.), "Oligonucleotides with reporter groups attached to the 5'–terminus," pp. 185–210, Oxford University Press (1991).

Smith M.R. et al., Cancer Gene Therapy, vol. 2 (3), "Antisense oligodeoxyribonucleotide down–regulation of bcl–2 gene expression inhibits growth of the low–grade non–Hodgkin's lymphoma cell line WSU–FSCCL," pp. 207–212 (1995).

Thuong and Asseline, *Oligonucleotides and Analogues—A Practical Approach*, F. Eckstein (Ed.), "Oligonucleotides attached to intercalators, photoreactive and cleavage agents," pp. 283–308, Oxford University Press (1991).

Tsujimoto Y. and Croce C., PNAS USA, vol. 83, "Analysis of the structure, transcripts, and protein products of bcl–2, the gene involved in human follicular lymphoma," pp. 5214–5218 (1986).

Zeigler A. et al., Journal of the National Cancer Institute, vol. 89 (14), "Induction of Apoptosis in Small–Cell Lung Cancer Cells by an Antisense Oligodeoxynucleotide Targeting the Bcl–2 Coding Sequence," pp. 1027–1036 (1997).

* cited by examiner

OLIGONUCLEOTIDE DERIVATIVES

The present invention relates to an oligonucleotide derivative directed against human Bcl-2 mRNA. The present invention further relates to a pharmaceutical composition comprising said oligonucleotide derivative, uses thereof and methods of treatment and diagnosis utilizing said oligonucleotide derivative.

Human Bcl-2 is a protein which is closely associated with the process of programmed cell death (apoptosis). Lack of programmed cell death plays an important role in cancer and other hyperproliferative diseases like restenosis, fibrosis or psoriasis, in particular in tumor progression and, importantly, might contribute to the clinical problem of resistance to anti-neoplastic regimens (standard chemotherapeutic drugs/gamma-irradiation).

Oligonucleotides or, in particular, oligonucleotide derivatives directed against human Bcl-2 mRNA may be used in an antisense technology strategy interferring with expression of Bcl-2. For example, it has been reported that such an approach results in decreased cell survival (L. Campos et al., Blood 84 (1994), pp. 595–600; F. E. Cotter et al, Oncogene 9 (1994), pp. 3049–3055; M. R. Smith et al., Cancer Gene Ther. 2 (1995), pp. 207–212), the induction of apoptotic death (F. J. Keith et al., Leukemia 9 (1995), pp. 131–138), and increased drug-sensitivity (S. Kitada et al., Antisense Res. Dev. 4 (1994), pp. 71–79; J. C. Reed et al., see above) in lymphoid tumor cells.

However, there is an ongoing need for further oligonucleotides or oligonucleotide derivatives showing high efficacy, preferably improved efficacy, in modulating the biosynthesis or expression of human Bcl-2, in particular for the treatment of hyperproliferative diseases, e.g. those as mentioned above.

Surprisingly, it has been found that the compounds according to the present invention, mentioned below, show the capability to modulate human Bcl-2 biosynthesis in a cell. They are therefore appropriate for the therapeutic treatment of diseases that respond to this modulation, especially inhibition, of Bcl-2 biosynthesis, such an inibition having as one effect an induction of apoptosis, resulting in inhibition of cell (hyper)proliferation.

In the context of the present invention it has been identified that a region encompassing nucleotide nos. 1880 to 1899, or encompassing at least a part thereof, of the coding region of a RNA deriving from the gene encoding human Bcl-2 protein, and the region comprising the translation termination codon, which codon encompasses nucleotides having nos. 2176 to 2178 of said RNA, are particularly accessible, for hybridization with an antisense oiigonucleotide or oligonucleotide derivative, in particular under physiological conditions for example as encountered in a cellular environment, resulting in modulation of the biosynthesis of the human Bcl-2 protein in a cell. Preferably, said region around the translation termination codon comprises nucleotide having nos. 2175 to 2194, or comprises at least a part thereof, of said RNA. In one aspect, the present invention relates to such an oligonucleotide derivative.

Accordingly, it is an object of the present application to provide an oligonucleotide derivative which is specifically hybridizable to a region of a RNA deriving from the gene encoding human Bcl-2 protein, said region being selected from the group consisting of a region comprising a sequence corresponding to a sequence ranging from base position no. 1880 (5') to no. 1899 (3'), or comprising at least a part thereof, of the human Bcl-2 cDNA, and a region comprising the translation termination codon of said RNA.

Within the context of the present invention, a RNA, deriving from the gene encoding human Bcl-2 protein, is pre-mRNA or, preferred, mRNA.

Within the context of the present invention, an oligonucleotide derivative is preferred, which is capable of modulating the biosynthesis of the human Bcl-2 protein.

A preferred embodiment thereof is directed to an oligonucleotide derivative as mentioned above, wherein said region is selected from the group consisting of a region comprising a sequence corresponding to a sequence ranging from base position no. 1880 (5') to 1899 (3') of the human Bcl-2 cDNA, and a region comprising the translation termination codon of said RNA, the former being preferred.

A likewise preferred embodiment thereof relates to an oligonucleotide derivative as mentioned above, wherein said region comprising the translation termination codon of said RNA comprises a sequence corresponding to a sequence ranging from base position no. 2175 (5') to 2194 (3'), or comprises at least a part thereof, of the human Bcl-2 cDNA. Preferably, said region comprising the translation termination codon of said mRNA comprises a sequence corresponding to a sequence ranging from base position no. 2175 (5') to 2194 (3') of the human Bcl-2 cDNA.

In an even more preferred embodiment thereof, said respective region consists of the respective sequence as specified, i.e. the sequence ranging from base position no. 1880 (5') to 1899 (3') of the human Bcl-2 cDNA, or the sequence ranging from base position no. 2175 (5') to 2194 (3') of the human Bcl-2 cDNA, the former being preferred.

Within the context of this invention, the term "oligonucleotide derivative" therefore preferably denotes an oligonucleotide which is structurally modified, as compared with a corresponding natural oligonucleotide, at at least one position of at least one building block (this can e.g. relate to the sugar or the base of a nucleoside building block, or to an internucleosidic bridging group). An oligonucleotide derivative can also comprise, in place of at least one nucleoside building block, at least one nucleoside analogue which encompasses a non-sugar backbone to which a nucleic acid base is linked.

Derivatized oligonucleotides, nucleosides, internucleosidic bridging groups and analogues have been described (cf., for example, De Mesmaeker, A. et al., Curr. Op. Struct. Biol. 5 (1995), pp. 343–355; Sanghvi, Y. S. et al., (Ed.), "Carbohydrate Modifications in Antisense Research", ACS Symposium Series 580 (1994); S. T. Crooke, "Therapeutic Applications of Oligonucleotides", R. G. Landes Company Publisher (1995)).

Within the context of the present invention, "modulation" of the biosynthesis or expression of the human Bcl-2 protein denotes an interference with the biosynthesis or expression, in particular a partial or complete inhibition thereof, in particular in connection with the translation or transcription process. Such an inhibition, in particular due to partial or complete degradation of the target nucleic acid, due to the process for translating the target nucleic acid being completely or partially inhibited, or due to the transcription process being completely or partially inhibited, can be determined by means of known methods, for example by means of the Northern blot technique at the level of the target nucleic acid, or by means of the Western blot technique at the protein level (cf., for example, Sambrook,J., Fritsch, E. F. and Maniatis, T.: "Molecular Cloning: A Laboratory Manual", 2nd Edition, Cold Spring Harbor Laboratory Press, 1989). For further means, reference is made to the Examples as mentioned below. In this connection, the term "hybridization" in particular denotes binding by way of hydrogen bonds, known as "Watson-Crick base-pairing", between complementary bases of an oligonucleotide derivative according to the invention, on the one hand, and of a target nucleic acid, on the other hand. "Specific hybridization" denotes that a sufficient degree of complementarity exists between the oligonucleotide derivative according to the invention and the target nucleic acid to enable specific binding between the oligonucleotide derivative and the nucleic acid to be achieved. In this context, it is not absolutely necessary, for achieving specific hybridization, for 100% or full complementarity to exist between the oligonucleotide derivative according to the invention and the target nucleic acid. An oligonucieotide derivative according to the invention hybridizes "specifically" with a target nucleic acid when the binding of the oligonucleotide to the target nucleic acid impairs the function of the latter and, furthermore, an adequate degree of complementarity is present in order to avoid non-specific binding of the oligonucleotide derivative according to the invention to a nucleic acid other than the target nucleic acid when specific binding is required, for example under physiological conditions in association with an in-vivo application, such as a therapeutic treatment.

Specific hybridization can be determined, for example, by means of an in-vitro hybridization assay, preferably under physiological conditions, between an oligonucleotide derivative according to the invention and a target nucleic acid. Appropriate reaction conditions are known (cf., for example, Sambrook, J., Fritsch, E. F. and Maniatis, T.: "Molecular Cloning: A Laboratory Manual", 2nd Edition, Cold Spring Harbor Laboratory Press, 1989, Vol.2, 9.47 to 9.58). In this context, further reference is made to those methods as described in the Examples, below.

The term "at least a part thereof" designates either (i) an internal part of the sequence as specified, said internal part having a length of at least 8 consecutive building blocks, or (ii) a terminal part of the sequence as specified, said terminal part comprising at least the 5'-terminal or the 3'-terminal nucleotide of the sequence ranging from nucleotide nos. 1880 to 1899, i.e. nucleotide no. 1880 or 1899, respectively, or of the sequence ranging from nucleotide nos. 2175 to 2194, i.e. nucleotide no. 2175 or 2194, respectively, or comprises up to the terminal 19 nucleotides of the 5'-end or of the 3'-end of any of said sequences. In this case the region, to which the oligonucleotide derivative is specifically hybridizable, encompasses an additional sequence, preferably of up to 20 building blocks, more preferably of up to 10 building blocks, immediately upstream (i.e. in 5'-direction) flanking the 5'-terminal nucleotide, or immediately downstream (i.e. in 3'-direction) flanking the 3'-terminal nucleotide, respectively, of the sequence as specified.

The term "corresponding to the sequence" denotes the relationship between the target nucleic acid, i.e. a human Bcl-2 RNA (i.e. pre-mRNA or, preferably, mRNA), against which an oligonucleotide derivative according to the present invention is directed, and the cDNA derived from that mRNA as described in the literature (see Y. Tsujimoto et al., Proc. Natl. Acad. Sci. USA 83 (1986), pp. 5214–5218, as mentioned above). The sequence of this cDNA is accessible in the GenBank data base under accession number M13994 GENBANK:HUMBCL2A. Within the context of the present application, the numbering of nucleic acids, in particular of cDNA sequences, relates to the respective numbering of the human Bcl-2 cDNA as contained in said data base under said accession number. Hence, a sequence of said mRNA "corresponds" to a sequence of said cDNA in the sense that said mRNA sequence can be deduced from said cDNA sequence, in particular by exchanging any base T of the cDNA sequence by a base U in the mRNA sequence.

Thus, the cDNA sequence ranging from nuctetotide nos. 1890 to 1899 reads as follows:

5'-GGGTGAACTGGGGGAGGATT-3' SEQ ID NO: 1.

The cDNA sequence of the translation termination codon, i.e. ranging from nucleotide nos. 2176 to 2178, reads as follows:

5'-TGA-3'.

The cDNA sequence ranging from nucleotide nos. 2175 to 2194 reads as follows:

5'-GTGAAGTCAACATGCCTGCC-3' SEQ ID NO: 2.

In another preferred embodiment the present invention is directed to an oligonucleotide derivative as mentioned above, comprising a base sequence selected from the group consisting of the base sequence 5'-AATCCTCCCCCAGTTCACCC-3' SEQ ID NO: 3, which corresponds to the sequence ranging from nucleotide nos. 1890 to 1899 of the human Bcl-2 cDNA, and the base sequence 5'-GGCAGGCATGTTGACTTCAC-3' SEQ ID NO: 4, which corresponds to the sequence ranging from nucleotide nos. 2175 to 2194 of human Bcl-2 cDNA, or a base sequence which is analogous thereto, or comprising at least a part of any of said base sequences, said oligonucleotide derivative being complementary to the corresponding sequence of a human Bcl-2 RNA, or comprising at least one mispairing or a basic building block.

Preferably, such an oligonucleotide derivative is specifically hybridizable to the corresponding region of a RNA deriving from the gene encoding human Bcl-2 protein., said RNA being, in particular, pre-mRNA, or, preferably, mRNA.

Also preferred, such an oligonucleotide derivative is capable of modulating the biosynthesis of human Bcl-2 protein.

In the context of the present application the term "complementary" denotes full complementarity between the base sequence of the oligonucleotide derivative and the target nucleic acid in the sense of Watson-Crick base pairing. Such full complementarity can be achieved by incorporating into the oligonucleotide derivative the respective complementary base sequence with regard to the target nucleic acid strand or a suitable analogous base sequence.

Within the context of the present invention, "analogous" base sequence denotes a base sequence in which one or more nucleic acid bases of the respective specified base sequence is/are been replaced by corresponding analogous nucleic acid bases, which retain the oligonucleotide derivative's capability of specific hybridization with the target nucleic acid. For example cytosine can be exchanged by 5-methylcytosine, or adenine by 2-aminoadenine, or, in a broader sense, a given base can be replaced by an inert base like hypoxanthine. Such analogous or inert bases are known to the skilled person and examples for such bases are mentioned below.

In the same context, the term "at least a part" is to be understood in a similar way as defined above.

Within the context of the present application the term "mispairing building block" denotes a building block of said oligonucleotide derivative which bears a nucleic acid base which is not the complemetary base with respect to the respective position of the target nucleic acid strand in the sense of Watson-Crick base pairing. For example, where in the target nucleic acid strand at a specific position the base A is located, the complementary base of the oligonucleotide derivative would be the base T, and a misparing building block can, for example, be the base C or the base G. In the same context the term "a basic building block" denotes a building block of said oligonucleotide derivative bearing no nucleic acid base capable of hybridization with the complementary base with respect to the respective position of the target nucleic acid strand in the sense of Watson-Crick base pairing. For example, an a basic building block can be a nucleoside unit solely consisting of a backbone (i.e. a sugar and an internucleosidic linkage) without comprising a nucleic acid base.

The incorporation of such a misparing or a basic building block into an oligonucleotide derivative can be tolerated as long as the resulting oligonucleoptide derivative is capable of specific hybridization with the target nucleic acid and, preferably, capable of modulating the biosynthesis of human Bcl-2 protein. Preferably, the oligonucleotide derivative according to the present invention comprises not more than up to 5 mispairing building blocks and/or not more that up to 3 a basic building blocks.

Preferred is such an oligonucleotide derivative comprising a base sequence selected from the group consisting of the base sequence 5'-AATCCTCCCCCAGTTCACCC-3' SEQ ID NO: 3, which corresponds to the complementary sequence of the sequence ranging from nucleotide nos. 1890 to 1899 of the human Bcl-2 cDNA, and the base sequence 5'-GGCAGGCATGTTGACTTCAC-3' SEQ ID NO: 4, which corresponds to the complementary sequence of the sequence ranging from nucleotide nos. 2175 to 2194 of human Bcl-2 cDNA, or a base sequence which is analogous thereto, said oligonucleotide derivative being complementary to the corresponding sequence of said RNA, or comprising at least one mispairing or a basic building block.

More preferred is such an oligonucleotide derivative, consisting of a base sequence selected from the group consisting of the base sequence 5'-AATCCTCCCCCAGTTCACCC-3' SEQ ID NO: 3, which corresponds to the complementary sequence of the sequence ranging from nucleotide nos. 1890 to 1899 of the human Bcl-2 cDNA, and the base sequence 5'-GGCAGGCATGTTGACTTCAC-3' SEQ ID NO: 4, which corresponds to the complementary sequence of the sequence ranging from nucleotide nos. 2175 to 2194 of human Bcl-2 cDNA, or of a base sequence which is analogous thereto, said oligonucleotide derivative being complementary to the corresponding sequence of said RNA, or comprising at least one mispairing or a basic building block.

Even more preferred is such an oligonucleotide derivative, consisting of a sequence selected from the group consisting of the base sequence 5'-AATCCTCCCCCAGTTCACCC-3' SEQ ID NO: 3, which corresponds to the sequence ranging from nucleotide nos. 1890 to 1899 of the human Bcl-2 cDNA, and the base sequence 5'-GGCAGGCATGTTGACTTCAC-3' SEQ ID NO: 4, which corresponds to the sequence ranging from nucleotide nos. 2175 to 2194 of human Bcl-2 cDNA, said oligonucleotide derivative being complementary to the corresponding sequence of said RNA, i.e. comprising no misparing and/or no a basic building blocks.

Particularly preferred is such an oligonucleotide derivative, consisting of the base sequence 5'-AATCCTCCCCCAGTTCACCC-3' SEQ ID NO: 3, which corresponds to the sequence ranging from nucleotide nos. 1890 to 1899 of the human Bcl-2 cDNA, said oligonucleotide derivative being complementary to the corresponding sequence of said RNA, i.e. comprising no mispairing and/or a basic building blocks.

An oligonucleotide derivative according to the present invention, i.e of any of the types as mentioned above, preferably comprises at least one building block of formula (I)

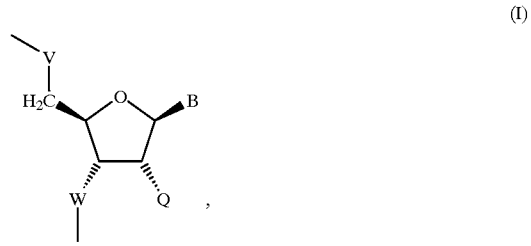

wherein

Q is H, —OCH$_3$, —OCH$_2$CH$_2$NR$_1$R$_2$, wherein R$_1$ and R$_2$ are, independently of each other, H or —CH$_3$, or, preferably, —O(CH$_2$CH$_2$)$_n$OCH$_3$, wherein n is 1, 2 or 3, preferably 1;

V and W are, independently of each other, the same or different radicals of an internucleosidic bridging group selected from the following group: 5'-O—P(O)(OH)—O-3' (phosphodiester), 5'-O—P(O)(SH)—O-3' (phosphorothioate), 5'-O—P(S)(SH)—O-3' (phosphodithioate), 5'-O—P(O)(CH$_3$)—O-3' (methylphosphonate), 5'-O—P(O)(NH—R$_7$)—O-3' (phosphoamidate) in which R$_7$ is C$_1$–C$_3$alkyl, 5'-O—P(O)(OR$_8$)—O-3' (phosphotriester) in which R$_8$ is C$_1$–C$_3$alkyl, 5'-O—S(O)$_2$—CH$_2$-3' (sulfonate), 5'-O—S(O)$_2$-NH—S(O)$_2$—CH$_2$-3' (sulfonamide), 5'-CH$_2$—S(O)$_2$—CH$_2$-3' (sulfone), 5'-O—S(O)—O-3' (sulfite), 5'-CH$_2$—S—(O)—CH$_2$- 3' (sulfoxide), 5'-CH$_2$—S—CH$_2$-3' (sulfide), 5'-O—CH$_2$—O-3' (formacetal), 5'-S—CH$_2$—O-3' (3'-thioformacetal), 5'-O—CH$_2$—S-3' (5'-thioformacetal), 5'-CH$_2$—CH$_2$—S-3' (thioether), 5'-CH$_2$—NH—O-3' (hydroxylamine), 5'-CH$_2$—N(CH$_3$)—O-3' (methylene(methylimino)), 5'-CH$_2$—O—N(CH$_3$)-3'(methyleneoxy(methylimino)), 5'-O—C(O)—NH-3' (5'-N-carbamate), 5'-CH$_2$—C(O)—NH-3' (amide), 5'-NH—C(O)—CH$_2$-3' (amide 2), 5'-CH$_2$-NH-C(O)-3' (amide 3) and 5'-C(O)—NH—CH$_2$-3' (amide 4), and the tautomeric forms thereof;

or one of V and W is such an internucleosidic bridging group and the other is a terminal radical selected from the group consisting of -OH and -NH$_2$, preferably -OH; and B is a radical of a nucleic acid base;

with the proviso that if Q is H, then at least one of V or W is an internucleosidic bridging group other than 5'-O—P(O)(OH)—O-3' (phosphodiester).

Within the context of the present invention, Q is preferably —OCH$_2$CH$_2$NR$_1$R$_2$, wherein one of R$_1$ and R$_2$ is H and the other is -CH$_3$, or each of R$_1$ and R$_2$ is H, or, more preferably, Q is —OCH$_2$CH$_2$OCH$_3$.

Oligonucleotide derivatives according to the present invention which comprise a building block of formula (I), wherein Q is other than H, can be prepared in accordance with the methods as described, for example, by P. Martin, Helv. Them. Acta, 78 (1995), pp. 486–504, or in an analogous way.

The 5' and 3' orientation of the said radicals V and W, as an internucleosidic bridging bond, in the above-mentioned formula (I), may be clarified as follows: When V for example is a radical 5'-CH$_2$—C(O)—NH-3' (amide), the corresponding nucleoside building block of the above-defined formula (I) has the following structure (I.1):

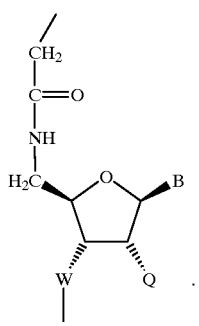

(I.1)

When W for example is a radical 5'-CH$_2$—C(O)—NH-3' (amide), the corresponding nucleoside building block of the above-defined formula (I) has the following structure (I.2):

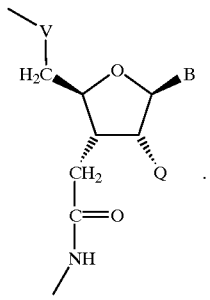

(I.2)

Some of the said radicals of internucleosidic bridging groups can exist in different tautomeric forms, depending, inter alia, on the solvent and on the degree of ionization of ionizable groups. Within the context of the present invention, the term "oligonucleotide derivative" also encompasses those tautomeric forms which are familiar to the skilled person.

Particularly preferably, V and W, as the radical of an internucleosidic bridging group, are selected, independently, from the following group: 5'O—P(O)(OH)—O-3' (phosphodiester), 5'-O—P(O)(SH)—O-3' (phosphorothioate) and 5'-CH$_2$—C(O)—NH-3' (amide).

In particular, one of the radicals V or W, as the radical of an internucleosidic bridging group, is 5'-O—P(O)(OH)—O-3' (phosphodiester) and the other radical is 5'-O—P(O)(SH)—O-3' (phosphorothioate).

V and W are also preferably, as the radical of an internucleosidic bridging group, in each case 5'-O—P(O)(OH)—O-3' (phosphodiester) or, mostly preferred, in each case 5'-O—P(O)(SH)—O-3' (phosphorothioate).

Preferred is an oligonucleotide derivative according to the present invention, comprising only building blocks of formula (I), wherein V and W each are phosphorothioate and Q is H.

Within the context of the present invention, a nucleic acid base, in particular a nucleic acid base B of formula (I), is understood as being, in particular, natural nucleic acid bases and known analogues (cf., for example, Accounts of Them. Res. 28 (1955), pp. 366–374; Sanghvi, Y. S. in: Antisense Research and Applications, Crooke, S. T. and Lebleu, B. (Ed.), CRC Press, Boca Raton (1993), pp. 273–288) As is familiar to the skilled person, nucleic acid bases B can exist in tautomeric forms depending on the ambient conditions. According to the invention, such tautomeric forms are also encompassed by the oligonucleotide derivatives according to the invention, including the preferred embodiments. The invention preferably relates to an oligonucleotide derivative according to the invention, including the said preferences, in which said nucleic acid base, in particular said nucleic acid base B of formula (i), is a radical of the formula (V1), (V2), (V3), (V4) or (V5)

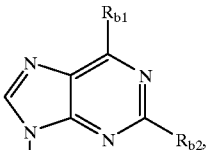

(V1)

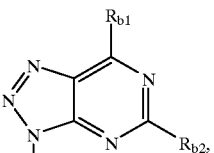

(V2)

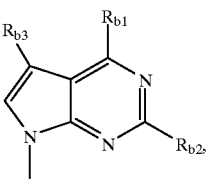

(V3)

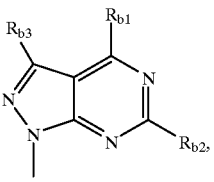

(V4)

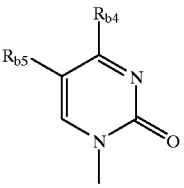

(V5)

in which $R_{b1}$ is —NH$_2$, —SH or —OH;

$R_{b2}$ is H, —NH$_2$ or —OH; and $R_{b3}$ is H, Br, I, —CN, —C≡C—CH$_3$, —C(O)NH$_2$ or —CH$_3$;

$R_{b4}$ is —NH$_2$ or —OH; and $R_{b5}$ is H, F, Br, I, —CN, —C≡C—CH$_3$, —C(O)NH$_2$ or -CH$_3$.

In a preferred embodiment thereof, said nucleic acid base, in particular said nucleic acid base B of formula (I), is a radical of the formula (V1) or (V5)

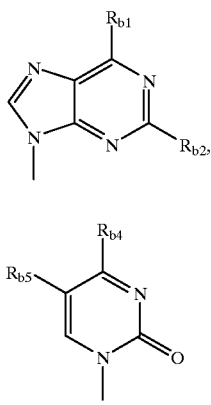

(V1)

(V5)

in which
R$_{b1}$ is —NH$_2$, —SH or —OH;
R$_{b2}$ is H, —NH$_2$ or —OH;
R$_{b4}$ is —NH$_2$ or —OH; and
R$_{b5}$ is H, F, Br, I, —CN, —C≡C—CH$_3$, —C(O)NH$_2$ or -CH$_3$.

Particularly preferably, said nucleic acid base, in particular said nucleic acid base B of formula (I), is selected from the group of the following radicals: xanthine, hypoxanthine, adenine, 2-aminoadenine, guanine, 6-thioguanine, uracil, thymine, cytosine, 5-methylcytosine, 5-propynyluracil, 5-fluorouracil and 5-propynylcytosine.

Preferred are oligonucleotide derivatives which (in their nucleotide/nucieotide derivative sequence) comprise at least one building block of formula (I), wherein B and Q are as defined herein, including the respective preferences and embodiments, and V and W are selected from the group consisting of the following radicals: 5'-O—P(O)(OH)—O-3' (phosphodiester), 5'-O—P(O)(SH)—O-3' (phosphorothioate) and 5'-CH$_2$—C(O)—NH-3' (amide), In case at least one of V or W is 5'-CH$_2$—C(O)—NH-3' (amide), the oligonucleotide derivative comprises preferably the following dimeric unit (bivalent radicals) of the formula (II)

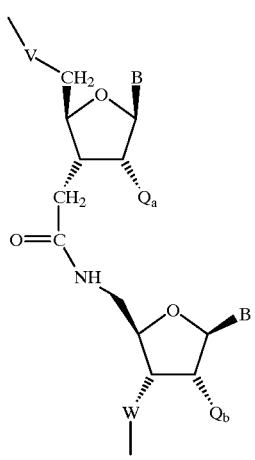

(II)

wherein Q$_a$ and Q$_b$ independently of each other, are H, —OCH$_3$ or —OCH$_5$CH$_2$OCH$_3$, or preferably Q$_a$ is —OCH$_3$ and Q$_b$ is H, or more preferably, Q$_a$ and Q$_b$ are each H;

and B, V and W are as defined herein, inclusive of the respective preferences and embodiments.

An oligonucleotide derivative according to the present invention, including the respective preferences and specific embodiments as mentioned herein, preferably consists of a total of 8 to 50, in particular of 8 to 22, particularly preferably of 10 to 20, more preferably of 15 to 20, even more preferably of 18, 19 or 20, and most preferably of 20 consecutive building blocks, preferably of the nucleoside type.

Mostly preferred is an oligonucleotide derivative according to the present invention, comprising only building blocks of formula (I), wherein each of V and W is phosphorothioate, Q is H, and the base sequence of said oligonucleotide derivative being selected from the group consisting of the base sequence 5'-AATCCTCCCCCAGTTCACCC-3' SEQ ID NO: 3, which corresponds to the complementary sequence of the sequence ranging from nucleotide nos. 1890 to 1899 of the human Bcl-2 cDNA, and the base sequence 5'-GGCAGGCATGTTGACTTCAC-3' SEQ ID NO: 4, which corresponds to the complementary sequence of the sequence ranging from nucleotide nos. 2175 to 2194 of human Bcl-2 cDNA, the former base sequence being particularly preferred. In other words, mostly preferred is the phosphorothioate analogue of an oligonucleotide derivative according to the present invention, which consists of a base sequence selected from the group consisting of the base sequence 5'-AATCCTCCCCCAGTTCACCC-3' SEQ ID NO: 3, which corresponds to the complementary sequence of the sequence ranging from nucleotide nos. 1890 to 1899 of the human Bcl-2 cDNA, and the base sequence 5'-GGCAGGCATGTTGACTTCAC-3' SEQ ID NO: 4, which corresponds to the complementary sequence of the sequence ranging from nucleotide nos. 2175 to 2194 of human Bcl-2 cDNA, the former base sequence being particularly preferred.

Preference is furthermore given to an oligonucleotide derivative according to the present invention which has a "chimeric" structure. Within the context of the present invention, a "chimeric structure", also termed a "chimera", is to be understood as meaning an oligonucleotide derivative which contains 2 or more chemically different regions which are in each case synthesized from one type of nucleic acid building block. Such chimeric oligonucleotide derivatives typically comprise at least one region of modified nucleic acid building blocks which confer one or more advantageous property/properties (for example increased resistance to nucleases, increased binding affinity or diminished occurrence of sequence-independent side-effects) on the oligonucleotide derivative, the so-called "wing", also designated the M region in that which follows, and a region which enables RNAse H-mediated cleavage of the target nucleic acid to take place, i.e. the so-called "RNAse H window", also designated the U region in that which follows. The affinity of an oligonucleotide or an oligonucleotide derivative is customarily determined by measuring the T$_m$ value of the oligonucleotide (derivative)/target nucleic acid hybrid. The T$_m$ value is the temperature at which the oligonucieotide, or its derivative, and the target nucleic acid dissociate from a previously formed hybrid. The dissociation is determined spectrophotometrically. The higher ther T$_m$ value, the higher is the affinity of the oligonucleotide, or the derivative, for the target nucleic acid. Methods for determining the T$_m$ value belong to the state of the art (cf., for example, Fritsch and Maniatis, "Molecular Cloning—A Laboratory Manual", 2nd Edition, Cold Spring Harbor Laboratory Press, 1989). Within the context of the present invention, increased resistance to nucleases denotes decreased or slowed-down degradation of the oligonucleotide derivatives according to the invention by exonucleases or endonucleases which are present in a cell. The resistance to nucleases or the degradation of an oligonucleotide or a derivative can be monitored by gel electrophoresis, for example. RNAse H is a cellular endonuclease which cleaves the RNA strand of an RNA:DNA duplex. Activation of the enzyme therefore leads to cleavage of the target RNA and consequently increases the efficacy of the antisense mechanism. Cleavage of the target RNA can customarily be demonstrated by gel electrophoresis. Since, in a chimera, different advantageous properties are present in one and the same molecule, oligonucleotide derivatives according to the invention possess a pronounced antisense effect with regard to inhibiting the expression of a protein or RNA.

In one embodiment, a chimeric oligonucleotide derivative according to the present invention comprises at least one M region, which consists of at least one nucleic acid building block of the formula (I) as mentioned above, and at least one U region, which enables RNAse H-mediated cleavage of the target nucleic acid to take place. The U region consists, in particular, of customary 2'-deoxyribonucleic acid building blocks which are linked to each other by way of phosphodiester bonds, or preferably phosphorothioate bonds, as the internucleosidic group. The M region of a chimeric oligonucleotide derivative according to the present invention consists, in particular, of nucleic acid building blocks of the formula (I) in which Q is as defined, preferably —OCH$_2$CH$_2$OCH$_3$, in which W and V, as the radical of an internucleosidic bridging group, are a phosphodiester bond, a phosphorothioate bond or an amide bond, with a phosphodiester bond being preferred.

Chimeric oligonucleotide derivatives according to the invention of the above mentioned type, which preferably consist of a total of 8 to 50, in particular of 8 to 22, particularly preferably of 10 to 20, more preferably of 15 to 20, even more preferably of 18, 19 or 20, and most preferably of 20 consecutive building blocks, preferably of the nucleoside type, preferably comprise one or more, preferably one, U region(s) having, for example, 4 to 10, preferably having from 6 to 8, nucleoside building blocks of formula III

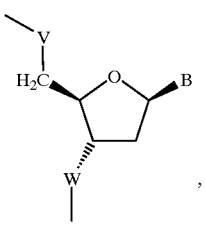

(III)

wherein B is as defined above, including the respective preferences and specific embodiments, and wherein V and W in each case are a phosphodiester group or phosphorothioate group, preferably a phosphorothioate group, as the radical of an internucleosidic bridging group, and further comprise one or more, preferably one or two, M region(s) comprising the remaining nucleoside building blocks, which are of formula (i), in which V and W are, as the radical of an internucleosidic bridging group, in particular, in each case, a phosphodiester, phosphorothioate or amide group, preferably phosphodiester or phosphorothioate, in particular phosphodiester, and in which Q and B are as defined above, including the respective preferences and specific embodiments, Q being in particular —O—CH$_2$CH$_2$OCH$_3$.

The M and U regions in chimeric oligonucleotide derivatives according to the invention are preferably present in one of the following arrangements:

5'-M—U—M-3'

5'-M—U-3' or

5'-U—M-3'.

Additional oligonucleotide derivatives according to the invention are conjugated with other units, for example a micelle-forming group, an antibody, a carbohydrate, a receptor-binding group, a steroid such as cholesterol, a polypeptide, an intercalating agent, such as an acridine derivative, a long-chain alcohol, a dendrimer, a phospholipid and other lipophilic groups. Conjugating in this way confers advantageous properties with regard to the pharmacokinetic characteristics on the oligonucleotide derivative according to the invention. In particular, conjugating in this way achieves increased cellular uptake.

In a very particularly preferred embodiment, an oligonucleotide derivative according to the present invention consists exclusively of nucleoside building blocks of the formula (I) which are connected to each other by way of phosphodiester bonds as the internucleosidic bridging groups V and/or W. In another very particularly preferred embodiment, an oligonucleotide derivative according to the invention exclusively comprises nucleoside building blocks of the formula Ili which are connected to each other by way of phosphorothioate bonds as the internucleosidic bridging groups V and/or W.

Provided that salt-forming groups are present, the term "oligonucleotide derivative" also encompasses salts, in particular acid addition salts, salts with bases or, if several salt-forming groups are present, possibly also mixed salts or internal salts. Salts of oligonucleotide derivatives according to the invention are, in particular, pharmaceutically tolerated salts, i.e. essentially nontoxic salts.

Such salts are formed, for example, from the oligonucleotide derivatives according to the invention which possess an acidic group, for example a carboxyl group, a phosphodiester group or a phosphorothioate group, and are, for example, salts with suitable bases. These salts include, for example, nontoxic metal salts which are derived from metals of groups Ia, Ib, IIa and IIb of the Periodic System of the elements, in particular suitable alkali metal salts, for example lithium, sodium or potassium salts, or alkaline earth metal salts, for example magnesium or calcium salts. They furthermore include zinc and ammonium salts and also salts which are formed with suitable organic amines, such as unsubstituted or hydroxyl-substituted mono-, di- or tri-alkylamines, in particular mono-, di- or tri-alkylamines, or with quaternary ammonium compounds, for example with N-methyl-N-ethylamine, diethylamine, triethylamine, mono-, bis- or tris-(2-hydroxy-lower alkyl)amines, such as mono-, bis- or tris-(2-hydroxyethyl)amine, 2-hydroxy-tert-butylamine or tris(hydroxymethyl)methylamine, N,N-di-lower alkyl-N-(hydroxy-lower alkyl)amines, such as N,N- dimethyl-N-(2-hydroxyethyl)amine or tri-(2-hydroxyethyl) amine, or N-methyl-D-glucamine, or quaternary ammonium compounds such as tetrabutylammonium salts.

Lithium salts, sodium salts, magnesium salts, zinc salts or potassium salts are preferred, with sodium salts being particularly preferred.

Oligonucleotide derivatives according to the invention which possess a basic group, for example an amino group or imino group, can form acid addition salts, for example with inorganic acids, for example with a hydrohalic acid, such as hydrochloric acid, sulfuric acid or phosphoric acid, or with organic carboxylic acids, sulfonic acids, sulfo acids or phospho acids or N-substituted sulfamic acid, for example acetic acid, propionic acid, glycolic acid, succinic acid, maleic acid, hydroxymaleic acid, methylmaleic acid, fumaric acid, malic acid, tartaric acid, gluconic acid, glucaric acid, glucuronic acid, citric acid, benzoic acid, cinnamic acid, mandelic acid, salicylic acid, 4-aminosalicylic acid, 2-phenoxybenzoic acid, 2-acetoxybenzoic acid, embonic acid, nicotonic acid or isonicotonic acid, and, in addition, with amino acids, for example with a-amino acids, and also with methanesulfonic acid, ethanesulfonic acid, 2-hydroxymethanesulfonic acid, ethane-t,2-disulfonic acid, benzenedisulfonic acid, 4-methylbenzenesulfonic acid, naphthalene-2-sulfonic acid, 2- or 3-phosphoglycerate, glucose-6-phosphate or N-cyclohexylsulfamic acid (with formation of the cyclamates) or with other acidic organic compounds, such as ascorbic acid.

Oligonucleotide derivatives according to the invention which possess both acidic and basic groups can also form internal salts. Oligonucleotide conjugates according to the invention which possess more than one group which is suitable for salt formation can also form mixed salts. It is only the pharmaceutically tolerated salts, which are nontoxic when used correctly, which are employed for therapeutic purposes and which are therefore preferred.

In a further embodiment the present invention relates to a process for preparing an oligonucleotide derivative according to the present invention, said process comprising incorporating at least one building block of formula (I) as mentioned above into the oligonucleotide derivative during oligonucleotide synthesis.

The compounds of the formula (I), wherein V and W each are a terminal group as defined above, are employed as nucleoside building blocks in the synthesis of the oligonucleotide derivatives according to the invention. The oligonucleotide derivatives according to the invention can be prepared, in a manner known per se, in accordance with a variety of methods, in DNA synthesis equipment which can be automated and which can be obtained commercially in conjunction with method protocols. For example, in the case of a phosphodiester group as the internucleosidic bridging group, the phosphotriester method, the phosphite triester method or the H-phosphonate method, which are familiar to the skilled person, can be used (cf., for example, Eckstein, F., "Oligonucleotides and Analogues, A Practical Approach", IRL Press (1991)).

In the case of the phosphite triester method, the approach can, for example, be to react, for example, a nucleoside building block of the formula (I), in which $V_a$ and $W_a$ are in each case —OH, with a protecting group reagent, for example 4,4'-dimethoxytriphenylmethyl chloride, to give a nucleoside of the formula (Ib)

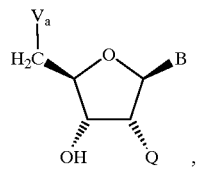

(Ib)

in which $V_a$ is a protected hydroxyl group and Q and B are defined as above for the compound of the formula I including the said preferences, reactive groups thereof being protected by a suitable protective group where necessary, and to bind the compound of the formula lb with the aid of a linker, for example succinic anhydride, to a solid support material, for example to "Controlled Pore Glass" (CPG), which contains long-chain alkylamino groups. In a separate procedure, the hydroxyl group of another nucleoside building block of the formula (Ib) is derivatized, for example using $R^xO$—$P[N(i-propyl)_2)]_2$ to give a phosphoramidite of the formula (Ic)

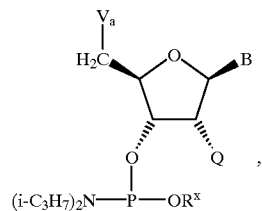

(Ic)

in which $R^x$ is a customary protecting group, for example β-cyanoethyl, wherein B and Q are defined above.

Protecting groups for the radical $V_a$ as protected hydroxyl group in compounds of the formulas (Ib) and (Ic) preferably are of the trityl-type, in particular trityl (Tr), 4-monomethoxytrityl (MMTr), preferably 4,4'-dimethoxytrityl (DMTr) and, likewise preferably, 4,4',4"-tris-tert-butyltrityl (TTTr).

After the protecting group on the radical $V_a$, for example the DMTr- or the TTTr group, of the support-bound material has been eliminated, this material is coupled, with elimination of —$N(i-C_3H_7)_2$ to the compound of the formula (Ic), any free hydroxyl groups which may be present are blocked ("capping") and the phosphite which has been formed is then oxidized, thereby leading, for example, to the phosphate or phosphorothioate. After the dimer has been deprotected, the reaction cycle is repeated with a compound of the formula (Ic) until an oligomer having the desired number of monomer units has been synthesized, and the product is then detached from the support material. In this way, an oligonucleotide derivative according to the invention is obtained which is synthesized entirely from nucleoside building blocks of the formula (I), above, having phosphodiester groups or phosphorothioate groups, depending on the oxidation conditions, as the internucleosidic bridging group. Depending on the use of appropriate nucleoside building blocks in the individual reaction cycles, oligonucleotides according to the invention of any arbitrary sequence can be prepared in an analogous manner, in particular those oligonucleotides according to the invention which, in addition to one or more nucleoside building block(s) of the formula (I), contain other nucleoside building blocks, in particular those comprising structures of formulas (II) and/or (III).

Oligonucieotide derivatives according to the present invention which do not contain, or which do not exclusively contain, phosphodiester groups or phosphorothioate groups as the internucleosidic bridging groups can be prepared in a manner known per se (cf., for example, the abovementioned publications of De Mesmaeker, A., or Crooke, S. T.).

The oligonucleotide derivatives according to the invention possess a number of advantageous properties. These include, in particular, a high binding affinity for a target nucleic acid and a high resistance to nucleases. Furthermore, they are capable of a sequence-specific effect, are taken up satisfactorily by a cell and have adequate bioavailability. These properties make the oligonucleotides according to the invention particularly suitable for pharmaceutical applications, in particular for modulating the biosynthesis or expression of the human Bcl-2 protein.

An oligonucleotide derivative according to the invention can be used, in particular, as an antisense oligonucleotide. The expression "antisense" is known to the skilled person and, in the context of the present invention, characterizes, in particular, the relationship between an oligonucleotide derivative according to the invention and the sequence, which is complementary to it, of a target nucleic acid (i.e human Bcl-2 pre-mRNA or, preferably, mRNA, namely that the oligonucleotide derivative and the complementary sequence are able to hybridize to each other. The identification of a suitable antisense oligonucleotide is a multi-step process. First of all, a target nucleic acid is identified which underlies the protein whose expression characterizes a pathological state in humans, and is to be modulated. In the present case, the target nucleic acid is, in particular, the RNA which is transcribed from the gene which encodes the protein of interest, such as pre-mRNA or, preferably, the (mature) mRNA. Within the target nucleic acid, a sequence or sequences is/are identified which interact, in particular by means of hybridization, with the oligonucleotide derivative according to the invention such that expression of the protein of interest is modulated. An oligonucleotide derivative according to the invention must possess a complementarity to the target nucleic acid which is adequate, due to sufficiently powerful and sufficiently specific hybridization, to achieve the desired effect.

Consequently, the invention also provides the use of an oligonucleotide derivative according to the invention, including the said preferences, as an antisense oligonucleotide.

According to the invention, oligonucleotide derivatives are preferred which are capable of modulating the expression (biosynthesis) of the human Bcl-2 protein.

The invention furthermore relates to a pharmaceutical composition which comprises an oligonucleotide derivative according to the invention, or a pharmaceutically tolerated salt thereof, in a pharmaceutically effective quantity, if desired together with a pharmaceutically tolerated excipient and/or auxiliary substance.

Pharmaceutical compositions according to the invention (and also oligonucleotide derivatives according to the invention) can be used, for example, for the therapeutic or prophylactic treatment of hyperplastic or neoplastic states, for example of cancer, in particular solid tumors, or of restenosis, fribrosis or psoriasis, preferably in a cancer selected from the group consisting of colorectal cancer, gastric cancer, prostate cancer, neuroblastoma, melanoma, thyroid cancer, renal cancer, breast cancer and, preferably, lung cancer, the letter being, for example, in particular NSCLC (non-small cell lung cancer) or, most preferably, SCLC (small cell lung cancer). In particular, pharmaceutical compositions according to the invention (and also oligonucleotide derivatives according to the invention) are capable of killing cancer cells, preferably by induction of apoptosis, and/or of reverting multidrug resistance of tumors.

Pharmaceutical compositions which are preferred in accordance with the invention comprise preferred oligonucleotide derivatives as described above.

The pharmaceutical compositions according to the invention are preferably present in the form of preparations which can be administered parenterally or of infusion solutions. Aqueous solutions of the active substance in water-soluble form, for example in the form of one of the abovementioned water-soluble salts, in the presence or absence of salts, such as NaCl, and/or pharmaceutically tolerated excipient materials, such as sugar alcohols, for example mannitol, are suitable, in particular, for parenteral administration, for example for intravenous or intraperitoneal administration. Aqueous suspensions for injection which comprise viscosity-increasing substances, such as sodium carboxymethyl cellulose, sorbitol and/or dextran, are also suitable for parenteral administration. These preparations or solutions are preferably isotonic aqueous solutions or suspensions. The active substance can be present, for example, in the form of a lyophilisate, if necessary together with a pharmaceutically tolerated excipient material, which lyophilisate is brought into solution, before its use for parenteral administration, by adding a suitable solvent. These solutions which are suitable for parenteral administration can also be employed as infusion solutions. The pharmaceutical compositions according to the invention can be sterilized and/or comprise auxiliary substances, for example preservatives, stabilizers, wetting agents and/or emulsifying agents, solubilizing agents, salts for regulating the osmotic pressure and/or buffers.

The pharmaceutical preparations, which, if desired, can comprise additional pharmacologically (or pharmaceutically) active compounds, for example antibiotics, are prepared in a manner known per se, for example by means of conventional solubilizing or lyophilizing methods, and comprise from about 0.0001% by weight to about 95% by weight, preferably from about 0.1% by weight, to about 90% by weight, in particular from about 0.5% by weight to about 30% by weight, for example from 1% by weight to 5% by weight, of active compound(s). Dosage forms in the form of individual doses comprise, for example, from about 0.001% by weight to about 20% by weight, of active compound(s); dosage forms which are not in the form of individual doses comprise, for example, from about 0.001% by weight to about 10% by weight of active compound(s). Dose units preferably comprise from about 0.0005 mg to about 0.5 mg, preferably from about 0.005 mg to about 40 mg of active compound(s), depending on the nature of the mammalian subject, including man, to be treated, on the disease to be treated and on the condition of the patient, in particular its/his/her body weight, its/his/her age and its/his/her individual state of health, and also on individual pharmacokinetics contributing factors and the route of administration.

In order to improve activity, the pharmaceutical compositions according to the invention can comprise cationic lipids.

Pharmaceutical compositions according to the invention are also preferred which additionally comprise a customary cytostatic agent. Such combination preparations are preferably employed for treating hyperplastic or neoplastic states such as cancer.

The present invention furthermore relates to an oligonucleotide derivative according to the invention, including the abovementioned preferences, or a pharmaceutically tolerated salt thereof, for use in the prophylactic or therapeutic treatment of humans, in particular of a pathological state, which is characterized by the expression or biosynthesis of human Bcl-2

The present invention furthermore relates to the use of an oligonucleotide derivative according to the invention, including the abovementioned preferences, for preparing a pharmaceutical composition for the prophylactic or therapeutic treatment of a pathological state in humans, which is characterized by the expression or biosynthesis of human Bcl-2 protein.

Over and above this, the present invention relates to a method for the prophylactic or therapeutic treatment of a pathological state in a mammalian subject, including man, which state is characterized by the expression or biosynthesis of human Bcl-2 protein, which method comprises administering a pharmaceutical composition according to the invention to man.

Moreover, the invention relates to a method for modulating the expression of human Bcl-2 protein in a cell, which comprises bringing the cell, or a tissue or body fluid which contains this cell, into contact with an oligonucleotide derivative according to the invention, including the abovementioned preferences, or with a pharmaceutical composition according to the invention. Such a process for modulating the expression or biosynthesis of a protein in a cell can be advantageously applied both in vitro and in vivo.

The oligonucleotide derivatives according to the invention, including the abovementioned preferences, are also suitable for use as diagnostic agents and can be employed, for example, in a manner known per se, as gene probes for detecting genetically determined diseases or viral infections by means of selective interaction at the level of single-stranded or double-stranded target nucleic acids. In particular, a diagnostic application is possible in vivo as well as in vitro, due to the increased stability towards nucleases. The diagnosis can take place, for example, on isolated tissue samples, blood plasma, blood serum or other body fluids, and, in the case of in-vivo diagnosis, on tissues, cells or body fluids in the patient to be investigated as well. In a preferred embodiment thereof, such diagnosis takes place under physiological conditions.

Another aspect of the present invention consequently relates to an oligonucleotide derivative according to the invention, including the abovementioned preferences, for use in a diagnostic method. As mentioned above, the oligonucleotide derivatives according to the invention are suitable both for in-vivo and for in-vitro diagnostic methods.

It is to note that the entire content of the references, patents and publications cited in this application is hereby incorporated by reference.

The following examples clarify the invention but do not restrict it. Examples are in particular directed to preferred embodiments of the present invention.

EXAMPLES

Example 1

Cell Culture

The SCLC cell lines (SW2, NCl-N417, NCl-H82, NCl-H69) are cultured in RPMI-1640 medium (Gibco Life Technologies, UK) supplemented with 2 mM I-glutamine, 10% fetal calf serum (FCS), 50 IU/ml penicillin and 50 ag/ml streptomycin at 37° C. in a humidified atmosphere with 5% CO2. The SW2 SCLC cell line have been obtained from Dr. S. D. Bernal, Dana Farber Cancer Institute, Boston, Mass., while NCl-N417, NCl-H82 and NCl-H69 cells have been obtained from the American Type Tissue Culture Collection (ATCC). All cells grow as floating aggregates.

Example 2

Synthesis of Oligonucleotide Derivatives

Phosphorothioate oligodeoxynucleotides according to the present invention are synthesized on a 0.5 mmole scale using a Milligen model 8800 DNA synthesizer (Bedford, Mass.) using modified phosphoramidite chemistries with β-cyanoethoxyphosphoramidites. Crude product of approximately 70% purity is further purified by orthogonal columns chromatography using a Millipore HC18-HA column followed by anion exchange chromatography using a Millipore Q-15 strong anion exchanger. The purified material is ethanol precipitated, redissoved and further desalted by ultrafiltration. The samples are depyrogenated by ultrafiltration with endotoxin levels reduced to below detectable levels using a standard endotoxin assay.

The following oligonucleotide derivaties (OD) are synthesized, all being 20-mer phosphorothioates purified by high pressure liquid chromatography (HPLC). The sequences are

OD1: 5'-AATCCTCCCCCAGTTCACCC-3' SEQ ID NO: 3

OD2: 5'-GGCAGGCATGTTGACTTCAC-3' SEQ ID NO: 4

The following oligonucleotide derivatives for use as scrambled controls (SC) to OD1 are likewise synthesised:

SC1: 5'-TCCCACCTCACCTACATCCG-3' SEQ ID NO: 5;

SC2: 5'-ACACCCCAATTCTTCCGCCC-3' SEQ ID NO: 6;

SC3: 5'-CTCATTCCTACCGACACCCC-3' SEQ ID NO: 7.

All oligonucleotide derivatives are kept at −20° C. in 10 mM Tris pH 7.4, 1 mM EDTA.

Example 3

Treatment of Cells with Oliconculeotide Derivatives

The oligonucleotide derivatives are delivered to cells in the form of complexes with the cationic lipid DOTAP (Boehringer Mannheim, Germany). Equal volumes of the respective oligonucleotide derivative (6 $\mu$M) and DOTAP (0.2 mM) in HEPES-buffered saline (HBS) are mixed and allowed to complex for 10 min at room temperature. The mixture is diluted into 9 volumes of RPMI-1 640 culture medium without FCS, and added to cells in culture medium containing 10% FCS to a final density of 2×105 cells/ml. The final concentrations are 0.15 $\mu$M ODNs and 5% FCS. Controls are treated with equivalent concentrations of DOTAP or medium alone. Cells are incubated at 37° C. for different periods of time, depending on the experiment. For higher oligonucleotide derivative concentrations, the charge ratio DOTAP:oligonucleotide derivative is maintained constant.

Example 4

Measurement of Cell Viability

The cytotoxicity of oligonucleotide derivatives on SCLC cells is determined by measurement of cell viability using the WST-1 cell proliferation reagent (Boehringer Mannheim), which detects the activity of a mitochondrial enzyme active only in living cells. For each treatment, 100 $\mu$l of cells/oligonucleotide derivative mixture are plated in triplicates in 96-well plates. Oligonucleotide derivative concentrations and cell densities are as described below. Cells are incubated for 96 h at 37° C., and then 10 μl of WST-1 reagent are added per well and allowed to react for 3 h at 37° C. Absorbance is measured at 450 nm using an ELISA reader (BIO-RAD model 2550 EIA reader). Data are expressed as percent of the absorbance of control treated cells.

Example 5

Detection of Bcl-2 mRNA by Northern Blot Analysis

Total RNA is prepared from 6×106 cells using the one step acid guanidinium isothiocyanate extraction method (see P. Chomczynski et al., Anal. Biochem. 162 (1987), pp. 156–159). Per sample, 10 μg total RNA are electrophoresed on denaturing formaldehyde-agarose gels and transferred to nylon membranes according to standard procedures (see J. Sambrook et al., Molecular Cloning: A Laboratory Manual, Cold Spring Harbor Laboratory Press, New York (1989)). Membranes are hybridized overnight at 42° C. with an EcoRI fragment composed of nucleotides 1410 to 2340 of the Bcl-2 cDNA which is radiolabelled with $^{32}$P using random hexanucleotide primers (Megaprime™ DNA labelling systems, Amersham). Simultaneous hybridization with a chicken β-actin probe is used for reference. Blots are exposed to a storage phosphor screen and scanned using a phosphorimager (Molecular Dynamics, Sunnyvale, Calif.).

Example 6

Detection of Bcl-2 Protein by Western Blot Analysis

For each treatment, 10 ml of cells/oligonucleotide derivative mixture are plated in a 25 cm2 flask and incubated for 24 h at 37° C. ODN concentrations and cell densities are as above. Soluble protein extracts are prepared as described (see M. Hanada et al., Cancer Res. 53 (1993), 4978–4986), and protein concentrations are determined using the BCA protein assay reagent (PIERCE, Rockford, Ill.). 100 μg of soluble protein per sample are separated on a 12% SDS polyacrylamide gel at 50 V for about 16 h. Electrotransfer to a polyvinylidene fluoride membrane (Hybond-PVDF, Amersham) is performed in a semi-dry blotting chamber (Schleicher and Schuell, Germany) at 1 mA/cm2 for 1 h. The blots are blocked in Tris-buffered saline (TBS) containing 5% BSA and 5% non-fat milk, and then incubated overnight at 4° C. with 200 ng/ml mouse anti-human Bcl-2 monoclonal antibody (DAKO Diagnostics AG, Glostrup, Denmark). To detect the primary antibody, blots are incubated with a rabbit anti-mouse IgG peroxidase conjugate (SIGMA Immunochemicals, St. Louis, Mo.) for 2 h at room temperature. Visualization of the immunocomplex is achieved by enhanced chemiluminescence using the ECLTM kit (Amersham), followed by exposure to X-ray film (FUJI RX). Relative protein levels are quantified after scanning of the autoradiograms (Hewlett Packard ScanJet Iicx) using the Imageouant software (Molecular Dynamics), and expressed as percent of the control.

Example 7

Detection of Apoptotic Cells Based on Light Scattering Properties and DNA Fragmentation Apoptosis is measured by flow cytometric quantification of DNA fragmentation after staining of nuclei with propidium iodide as described (see 1. Nicoletti et al., J. Immunol. Methods 139 (1991), pp.271–279), and by simultaneous analysis of cell morphology based on light scattering properties (see T. G. Cotter et al., 1992, Cancer Res. 52 (1992), pp. 997–600). Briefly, approximately 0.2×106 of ODN-treated cells are fixed in 2% paraformaldehyde and then permeabilized in 0.05% Triton-X100. Cells are resuspended in 0.5 ml of 50 μg/ml propidium iodide in PBS, and incubated in the dark for 15 min at room temperature. Cell-associated fluorescence is measured using a FACSCalibur cytofluorometer (Becton Dickinson, Mountain View, Calif.) equipped with a 4 log-decade full-scale amplifier gain, and an analogue-to-digital converter with 1024 channels. Apoptotic cells are visualized in contour plots, while quantitation is based on DNA fragmentation.

Example 8

Determination of Viable Cell Numbers by Propidium Iodide Exclusion and Light Scattering Properties Approximately 0.2×106 cells are briefly trypsinized and resuspended in PBS. Immediately before measurement, propidium iodide is added to a final concentration of 10 μg/ml, and the number of cells is measured by FACS analysis. Based on their morphology, cells are considered intact if they localized to the lower right quadrant of the contour plot (T. G. Cotter et al., 1992, see above). Within this area, only cells that exclude propidium iodide are considered viable.

Example 9

Determination of Basal Levels of Bcl-2 Expression in SCLC Cell Lines

To obtain information on human Bcl-2 expression, the four SCLC cell lines as decribed above are examined by Northern and Western blot analysis as indicated above. mRNA is expressed in all cell lines, with SW2 cells displaying the highest levels. However, Bcl-2 protein levels do not correlate with mRNA expression. Bcl-2 protein can be readily detected in SW2 and NCl-H69 cells, while faint bands can be seen in NCl-H82 and NCl-N417 cells only after overexposure of the film. In the latter cell lines, Bcl-2 levels appears to be expressed at the limit of detection by Western blot analysis. SW2 cells are used in subsequent experiments, as they express intermediate and readily detectable Bcl-2 protein levels.

Example 10

Effects of Oliaonucleotide Derivatives OD1 and OD2 on the Viabilitv of SW2 SCLC Cells To assess whether oligonucleotide derivatives acording to the present invention might be potent inhibitors of SCLC cell growth, 2 20-mer phosphorothioates directed against the coding region or the translation termination site of the Bcl-2 mRNA are synthesized, i.e OD1 and OD2, respectively. The oligonucleotide derivatives are first tested for their effect on SW2 cell viability using the WST-1 proliferation assay, as described above. Delivery of oligonucleotide derivatives to cells is achieved with the aid of the cationic lipid DOTAP. Cells are incubated for 96 h with 0.15 μM ODN; controls received medium alone or 5 mM DOTAP. Cells are incubated for 3 h with WST-1 reagent, and absorbance at 450 nm is measured. The two oligonucleotide derivatives OD1 and OD2 affect cell viability. OD2, directed against the translation termination site, causes a significant reduction of cell viability, and OD1, which targets codons 141–147 of the Bcl-2 mRNA, is even more cytotoxic, reducing the viability to 10% relative to control-treated cells.

Example 11

Effect of OD1 on Bcl-2 Levels

Non-specific toxicity of antisense oligonucleotides remains a major problem. Thus, sequence-specific down-regulation of the target protein or mRNA must be demonstrated. Therefore, Western blot analysis is performed to detect Bcl-2 protein levels after treatment of SW2 cells with oligonculeotide derivatives. Northern blot analysis is not used due to insufficient sensitivity, since Bcl-2 mRNA levels are relatively low in SCLC cells as compared to lymphoid tumor cells. Cells are incubated for 24 h with either 0.15 µM oligonucleotide derivative, 5 mM DOTAP, or medium alone. 100 µg of soluble protein are used for Western blot analysis. OD1 causes a significant reduction in Bcl-2 levels already at 24 h. A similar reduction is caused by OD2. To further test if the oligonucleotide derivatives cause a reduction at later time points, Western blot analysis is performed after incubation of cells for 96 h under the same conditions as above. At this time, OD1 causes marked reduction in Bcl-2 levels. As revealed by quantification of the relative protein levels from the x-ray films, OD1 reduces Bcl-2 by 81% at 24 h, and by 50% at 96 h, as compared to the control. Reductions of 68% and 5% are measured for OD2 at 24 h and 96 h, respectively.

To provide further evidence for the sequence-specific action of OD1, three control ODNs are synthesized with the same base composition but in scrambled order, i.e. SC1, SC2 and SC3, as indicated above. A gene-bank search reveales no homology of the scrambled ODNs to mammalian genes. To test their effect, various doses of each oligonucleotide derivative are added to SW2 cells, and Bcl-2 levels are measured by Western blot analysis. Cells are incubated for 24 h with medium alone, DOTAP (5 mM, 10 mM, and 15 mM), or the oligonucleotide derivatives (0.15 µM (not tested with SC1), 0.30 µM, and 0.45 µM). The control oligonucleotide derivatives (SC1, SC2 and SC3) alter Bcl-2 levels only marginally. Similarly, DOTAP shows no effect at either concentration. In contrast, OD1 causes a dose-dependent reduction in Bcl-2 protein. Quantification of relative protein levels reveal reductions of 60%, 70% and 77% for OD1 at 0.15 µM, 0.30 µM, and 0.45 µM, respectively. Comparable results are obtained when the same concentrations of oligonucleotide derivatives are tested for an effect on the viability of SW2 cells. WST-1 proliferation assays are performed as described above after incubation of SW2 cells for 96 h with the different oligonucleotide derivatives. OD1 causes a dose-dependent reduction in cell viability, while the scrambled controls are not toxic. Taken together, these results provide strong evidence for the ability of OD1 to reduce Bcl-2 levels and cell viability of SW2 SCLC cells by a sequence-specific mechanism.

Example 12
Induction of Massive and Dose-dependent Apoptotic Death in SW2 SCLC Cells Caused by OD1

To test whether down-regulation of Bcl-2 reduces cell viability by the induction of apoptosis in SCLC cells, flow cytometric analysis is performed to identify apoptotic cells based on their light scattering properties and DNA fragmentation. SW2 cells are treated for 72 h with medium alone, DOTAP (5 mM, 10 mM, and 15 mM), or oligonucleotide derivatives (0.15 µM, 0.30 µM, and 0.45 µM). After fixation and permeabilization, cells are incubated with propidium iodide and subjected to FACS analysis. Plotting the results as forward scatter (cell size) against side scatter (granularity) allows the identification of morphologically intact cells, apoptotic bodies, and apoptotic cells (see T. G. Cotter et al., 1992, as mentioned above). Control-treated cells localize to the lower right quadrant, and no significant difference is observed in the contour plots corresponding to DOTAP- and SC3-treated cells, irrespective of the concentrations used. Comparable results are obtained with SC1 and SC2. In contrast, a dose-dependent increase in the fraction of apoptotic cells (upper right quadrant) is induced by OD1. At the highest concentration, few morphologically intact cells are detectable. This result indicates that OD1 reduces SW2 cell viability by the induction of apoptosis, and that this process is dose-dependent.

Quantification of the above results based on DNA fragmentation, does not reflect the strong apoptotic effect detected by light scattering analysis. In the untreated control, 0.8% of apoptotic cells are measured. Depending on the concentration, in DOTAP- and SC3-treated cells values range from 0.8% to 0.9%, and from 1.1% to 1.4%, respectively, indicating a minimal effect. Treatment with OD1 increases the percentage of apoptotic cells to 2.3% at 0.15 µM, 5.9% at 0.30 4µM, and 8.2% at 0.45 µM, confirming nevertheless the dose-dependence of this process. The distribution of cells in the contour plots, however, would predict this numbers to be significantly higher. A possible explanation for this discrepancy could be that apoptosis in SCLC cells is not accompanied by complete degradation of DNA. This view is strengthened by a report indicating that apoptosis in epithelial cells, including a lung cell line, occurs in the absence of major internucleosomal fragmentation (F. Oberhammer et al., EMBO J. 12 (1993), pp. 3679–3684. Therefore, propidium iodide exclusion analysis is performed to obtain more accurate numbers of viable cells. Quantitation is done by FACS analysis after 24 h, 48 h, 72 h, and 96 h of incubation with two different concentrations (15 µM and 30 µM) of oligonucleotide derivatives. OD1 causes a strong inhibition of cell growth, which is apparent already after 48 h. Moreover, at the highest concentration (0.30 µM) it completely abolishes cell proliferation, as shown by a steady decrease in the number of viable cells. The number of viable cells is reduced to 28% and 5% of control values after 96 h of treatment with 0.15 µM and 0.30 µM OD1, respectively. This confirms that OD1 causes massive apoptosis of SW2 cells, in agreement with the results obtained by light scattering analysis.

Example 13
Decrease of Cell Viability of Various SCLC Cell Lines with OD1

The results described so far strongly support the cytotoxic potency of OD1 on the cell line cell line SW2, the viability of which is reduced to 10%. The effect of OD1 on the viability of three further SCLC cell lines (NCl-H82, NCl-H69, and NCl-N417) is tested using the WST-1 cell proliferation assay. These cell lines express Bcl-2 protein at various basal levels. For viability measurements, cells are incubated for 96 h with either medium alone, 5 mM DOTAP, or 0.15 µM ODNs. OD1 is cytotoxic to all cell lines tested, with variations in sensitivity among the cell lines. NCl-H69 cells are the most resistant, their viability being reduced to 19% of the untreated control value after treatment with OD1, and the viability of NCl-H82 and NCl-N417 cells is completely depressed. This indicates that OD1 is cytotoxic to a wide range of SCLC cell lines which depend on the life-sustaining function of Bcl-2 for survival.

What is claimed is:

1. A compound which is selected from the group consisting of the base oligonucleotide sequences 5'-AATCCTCCCCCAGTTCACCC-3', SEQ ID NO: 3; and 5'-GGCAGGCATGTTGACTTCAC-3', SEQ ID NO: 4; said oligonucleotide being complementary to the corresponding sequence of human Bcl-2 RNA.

2. A compound of claim 1 which is 5'-MTCCTCCCCCAGTTCACCC-3', SEQ ID NO: 3.

* * * * *

UNITED STATES PATENT AND TRADEMARK OFFICE
CERTIFICATE OF CORRECTION

PATENT NO.   : 6,291,668 B1
DATED        : September 18, 2001
INVENTOR(S)  : Ziegler et al.

It is certified that error appears in the above-identified patent and that said Letters Patent is hereby corrected as shown below:

<u>Column 26,</u>
Line 25, should read, -- 5'-AATCCTCCCCCAGTTCACCC-3', SEQ ID NO: 3. --

Signed and Sealed this

Thirtieth Day of April, 2002

Attest:

JAMES E. ROGAN
*Director of the United States Patent and Trademark Office*

*Attesting Officer*

SEQUENCE LISTING

<160> NUMBER OF SEQ ID NOS: 7

<210> SEQ ID NO 1
<211> LENGTH: 20
<212> TYPE: DNA
<213> ORGANISM: Artificial Sequence
<220> FEATURE:
<223> OTHER INFORMATION: Description of Artificial Sequence:Isolated
      polynucleotide
<223> OTHER INFORMATION: corresponding to nucleotide nos 1890 to 1899 of
      GenBank database accession number M13994
      GENBANK:HUMBCL2A

<400> SEQUENCE: 1
gggtgaactg ggggaggatt                                             20

<210> SEQ ID NO 2
<211> LENGTH: 20
<212> TYPE: DNA
<213> ORGANISM: Artificial Sequence
<220> FEATURE:
<223> OTHER INFORMATION: Description of Artificial Sequence:Isolated
      polynucleotide
<223> OTHER INFORMATION: Corresponds to nucleotide nos. 2175 to 2194 of
      GenBank accession number M13994 GENBANK:HUMBCL2A.

<400> SEQUENCE: 2
gtgaagtcaa catgcctgcc                                             20

<210> SEQ ID NO 3
<211> LENGTH: 20
<212> TYPE: DNA
<213> ORGANISM: Artificial Sequence
<220> FEATURE:
<223> OTHER INFORMATION: Derivative of SEQ ID NO:1

<400> SEQUENCE: 3
aatcctcccc cagttcaccc                                             20

<210> SEQ ID NO 4
<211> LENGTH: 20
<212> TYPE: DNA
<213> ORGANISM: Artificial Sequence
<220> FEATURE:
<223> OTHER INFORMATION: Description of Artificial Sequence:isolated
      polynucleotide
<223> OTHER INFORMATION: Derivative of SEQ ID NO:2

<400> SEQUENCE: 4
ggcaggcatg ttgacttcac                                             20

<210> SEQ ID NO 5
<211> LENGTH: 20
<212> TYPE: DNA
<213> ORGANISM: Artificial Sequence
<220> FEATURE:
<223> OTHER INFORMATION: Description of Artificial Sequence:isolated
      polynucleotide

<400> SEQUENCE: 5
tcccacctca cctacatccg                                             20

<210> SEQ ID NO 6
<211> LENGTH: 20
<212> TYPE: DNA
<213> ORGANISM: Artificial Sequence

```
<220> FEATURE:
<223> OTHER INFORMATION: Description of Artificial Sequence:isolated
      polynucleotide

<400> SEQUENCE: 6
acaccccaat tcttccgccc                                              20

<210> SEQ ID NO 7
<211> LENGTH: 20
<212> TYPE: DNA
<213> ORGANISM: Artificial Sequence
<220> FEATURE:
<223> OTHER INFORMATION: Description of Artificial Sequence:isolated
      polynucleotide

<400> SEQUENCE: 7
ctcattccta ccgacacccc                                              20
```